(12) United States Patent
Soliman et al.

(10) Patent No.: US 11,608,331 B2
(45) Date of Patent: Mar. 21, 2023

(54) ANTI-SARS COV-2 INHIBITORS BY DUAL VIRAL-HOST TARGETING

(71) Applicant: University of Sharjah, Sharjah (AE)

(72) Inventors: Sameh S. M. Soliman, Sharjah (AE); Bahgat Fayed, Sharjah (AE); Rania Hamdy, Sharjah (AE); Ahmed M. Almehdi, Sharjah (AE)

(73) Assignee: UNIVERSITY OF SHARJAH, Sharjah (AE)

( * ) Notice: Subject to any disclaimer, the term of this patent is extended or adjusted under 35 U.S.C. 154(b) by 8 days.

(21) Appl. No.: 17/339,349

(22) Filed: Jun. 4, 2021

(65) Prior Publication Data
US 2022/0402905 A1    Dec. 22, 2022

(51) Int. Cl.
| C07D 417/12 | (2006.01) |
| A61P 31/14 | (2006.01) |
| C07D 413/14 | (2006.01) |
| C07D 413/12 | (2006.01) |

(52) U.S. Cl.
CPC ............ C07D 417/12 (2013.01); A61P 31/14 (2018.01); C07D 413/12 (2013.01); C07D 413/14 (2013.01)

(58) Field of Classification Search
CPC ...... C07D 417/12; C07D 413/14; A61P 31/14
USPC ......................................................... 514/274
See application file for complete search history.

(56) References Cited

PUBLICATIONS

Huang et al., "Clinical features of patients infected with 2019 novel coronavirus in Wuhan, China", The Lancet, vol. 395, Feb. 15, 2020, pp. 497-506, 10 pages.
Zhang et al., "Therapeutic and triage strategies for 2019 novel coronavirus disease in fever clinics". The Lancet, vol. 8, Mar. 2020, pp. e11-e12, 2 pages.
Li & De Clercq, "Therapeutic options for the 2019 novel coronavirus (2019-nCoV)", Nature Reviews, Drug Discovery, vol. 19, Mar. 2020, pp. 149-150, 2 pages.
Amawi et al., "COVID-19 pandemic: an overview of epidemiology, pathogenesis, diagnostics and potential vaccines and therapeutics", Therapeutic Delivery, vol. 11, Issue 4, 2020, pp. 245-268, 24 pages.
Vankadari, "Arbidol: A potential antiviral drug for the treatment of SARS-CoV-2 by blocking trimerization of the spike glycoprotein", ELSEVIER, International Journal of Antimicrobial Agents, vol. 56, 2020, pp. 1-3, 3 pages.
Mostafa et al., "FDA-Approved Drugs with Potent In Vitro Antiviral Activity against Severe Acute Respiratory Syndrome Coronavirus 2", MDPI, Pharmaceuticals, vol. 13, Issue 443, 2020, pp. 1-24, 24 pages.
Lu, "Drug treatment options for the 2019-new coronavirus (2019-nCoV)", BioScience Trends, vol. 14, Issue 1, 2020, pp. 69-71, 3 pages.
Elfiky & Azzam, "Novel guanosine derivatives against MERS CoV polymerase: An in silico perspective", Journal of Biomolecular Structure and Dynamics, vol. 39, Issue 8, 2021, pp. 2923-2931, 9 pages.
Elmezayen et al., "Drug repurposing for coronavirus (COVID-19): in silico screening of known drugs against coronavirus 3CL hydrolase and protease enzymes", Journal of Biomolecular Structure and Dynamics, vol. 39, Issue 8, 2021, pp. 2980-2992, 13 pages.
Ghosh et al., "Drug Development and Medicinal Chemistry Efforts toward SARS-Coronavirus and Covid-19 Therapeutics", ChemMedChem, European Chemical Societies Publishing, vol. 15, 2020, pp. 1-27, 27 pages.
Hegyi and Ziebuhr, "Conservation of substrate specificities among coronavirus main proteases", Journal of General Virology, vol. 83, 2002, pp. 595-599, 5 pages.
Wu et al., "Analysis of therapeutic targets for SARS-CoV-2 and discovery of potential drugs by computational methods", ELSEVIER, Acta Pharm Sin B., vol. 10, Issue 5, 2020, pp. 766-788, 24 pages.
Walls et al., "Structure, Function, and Antigenicity of the SARSCoV-2 Spike Glycoprotein", Cell Press, vol. 181, Issue 2, 2020, pp. 281-292, 19 pages.
Coutard et al., "The spike glycoprotein of the new coronavirus 2019-nCoV contains a furinlike cleavage site absent in CoV of the same clade", ELSEVIER, ScienceDirect, Antiviral Research, vol. 176, Article 104742, 2020, 5 pages.
Xia et al., "The role of furin cleavage site in SARS-CoV-2 spike protein-mediated membrane fusion in the presence or absence of trypsin", Signal Transduction and Targeted Therapy 5, vol. 92, 2020, 3 pages.
de Greef et al., "Protective role for the N-terminal domain of α-dystroglycan in Influenza A virus proliferation", PNAS, vol. 116, Issue 23, 2019, pp. 11396-11401, 6 pages.
Zhang et al., "Crystal structure of SARS-CoV-2 main protease provides a basis for design of improved α-ketoamide inhibitors", Science, vol. 368,, Issue 6489, 2020, pp. 409-412, 5 pages.
Nair & Jacob, "A simple practice guide for dose conversion between animals and human", Journal of Basic and Clinical Pharmacy, vol. 7, Issue 2, 2016, pp. 27-31, 5 pages.
Shi et al., "Genetically Engineered Cell-Derived Nanoparticles for Targeted Breast Cancer Immunotherapy", Molecular Therapy, American Society of Gene & Cell Therapy, vol. 28, Issue 2, 2020, pp. 536-547, 12 pages.
Henrich et al., "The crystal structure of the proprotein processing proteinase furin explains its stringent specificity", Nature Structural & Molecular Biology, vol. 10, 2003, pp. 520-526.
Deng et al., "Discovery of structurally diverse HIV-1 integrase inhibitors based on a chalcone pharmacophore", Bioorganic & Medicinal Chemistry, vol. 15, Issue 14, 2007, pp. 4985-5002.
Soliman et al., "Selective inhibition of Rhizopus eumelanin biosynthesis by novel natural product scaffold-based designs caused significant inhibition of fungal pathogenesis", Biochemical Journal, vol. 477, Issue 13, 2020, pp. 2489-2507, 19 pages.

(Continued)

*Primary Examiner* — Kahsay Habte
(74) *Attorney, Agent, or Firm* — Hayes Soloway PC

(57) ABSTRACT

The present invention discloses novel SARS-CoV-2 inhibitors for therapeutic formulations and methods for treating SARS-CoV-2 infections. The compounds exhibit unique pharmacophoric features including conformational flexibility and spatial orientation within the binding sites of the targeted proteases. The present invention also discloses methods for treating SARS-CoV-2 infections, comprising administering to the subject in need thereof a therapeutically effective amount of the compound, or a pharmaceutically acceptable salt thereof, and one or more pharmaceutical excipients.

5 Claims, 11 Drawing Sheets

(56) References Cited

PUBLICATIONS

Fu et al., "Both Boceprevir and GC376 efficaciously inhibit SARS-CoV-2 by targeting its main protease", Nature Communications, vol. 11, Article No. 4417, 2020, 8 pages.
Gao et al., "Crystal structure of SARS-CoV-2 papain-like protease", Acta Pharmaceutica Sinica B, vol. 11, Issue 1, 2021, pp. 237-245, 10 pages.
Cheng et al., "Furin Inhibitors Block SARS-CoV-2 Spike Protein Cleavage to Suppress Virus Production and Cytopathic Effects", Cell Reports, vol. 33, Issue 2, Article 108254, 2020, 18 pages.
Soliman et al., "Effective targeting of breast cancer cells (MCF7) via novel biogenic synthesis of gold nanoparticles using cancer-derived metabolites", PLOS ONE, vol. 15, Issue 10, 2020, 16 pages.
Soliman et al., "Critical discovery and synthesis of novel antibacterial and resistance-modifying agents inspired by plant phytochemical defense mechanisms", ELSEVIER, ScienceDirect, Chemico-Biological Interactions, vol. 333, 2021, 12 pages.
Prevention CfDCa. Coronavirus Disease 2019. CDC Website CDC; 2020, https://www.cdc.gov/coronavirus/2019-ncov/index.html.

| Candidate inhibitor | Compound supplier ID | Percent inhibition against | |
|---|---|---|---|
| | | $M^{pro}$ | PLpro |
| Compound 1 | MCULE-5559121280-0 | 26.44 ±1.91 | 15.6±0.4 |
| Compound 2 | Molport-002-542-400 | 0±0 | 43.1±0.7 |
| Compound 3 | MCULE-8748749803-0 | 12±1.1 | 0±0 |
| Compound 4 | Molport-004-271-700 | 0±0 | 0±0 |
| Compound 5 | MCULE-4469963687-0 | 3.6±0.005 | 0±0 |
| Compound 6 | Molport-007-594-574 | 0±0 | 0.53±0 |
| Compound 7 | MCULE-3732245601-0 | 31±2 | 56.4±0.3 |
| Compound 8 | Molport-004-251-833 | 0±0 | 39.1±1.7 |
| Compound 9 | MCULE-3135581181-0 | 0±0 | 21.8±0.1 |
| Compound 10 | Moloport-005-550-475 | 0±0 | 0±0 |
| Compound 11 | MCULE-4485704859-0 | 0±0 | 0±0 |
| Compound 12 | MolPort-005-115-349 | 5.47±0.08 | 31.8±0.6 |
| Compound 13 | MCULE-7013373725-0 | 69.8±3.3 | 80±4.1 |
| Compound 14 | MCULE-4934649484-0 | 0±0 | 0±0 |
| Compound 15 | MCULE-2167531027-0 | 10.2±0.2 | 0±0 |
| Compound 16 | MCULE-3570302261-0 | 10.5±0.2 | 0±0 |
| CG376 | | 100±2.1 | |
| GRL0617 | | | 100±3.1 |

FIG. 1

| Compound | IC$_{50}$ (µM) against | | | | |
|---|---|---|---|---|---|
| | M$^{pro}$ | PLpro | Furin | SARS-CoV-2 virus | Mammalian cells (Toxicity) |
| 7 | 0.45 | 0.085 | 0.29 | 0.77 | 1.67 |
| 13 | 0.11 | 0.063 | 0.29 | 0.11 | 0.41 |

FIG. 2

4-[2-(2-{[)6-Hydroxy-2,4-dioxop1,2,3,4-tetrahydro-pyrmidin-5-yl)-[4-hydroxy-3-methoxy-phenyl)-methyl]-amino-4-oxo-4,5-dihydro-thiazol-5-yl)-acetylamino]-benzoic acid 1,2,5-Oxadiazole-3-carboximidic acid, 4,4'-(methylenediimino)bis,bis[[(2-hydroxyphenyl)methylene]hydrazide

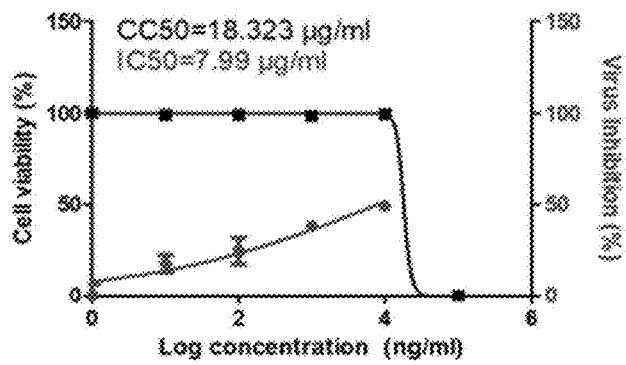
FIG. 10A
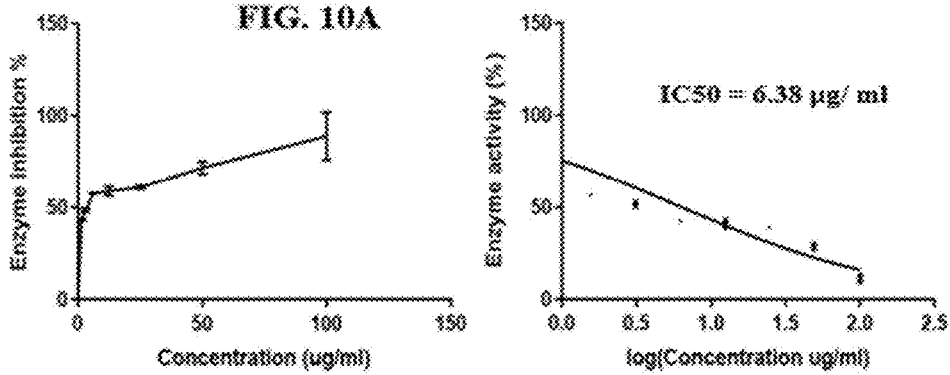
FIG. 10B     FIG. 10C
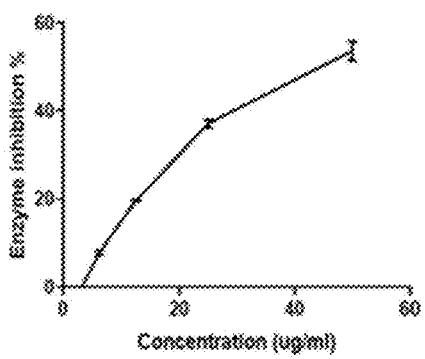 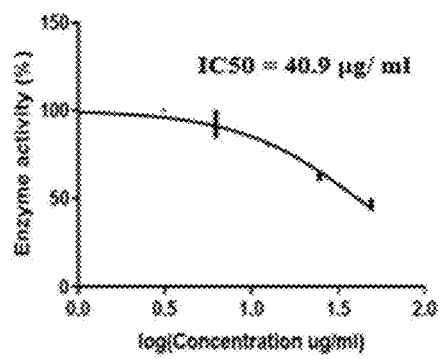
FIG. 10D     FIG. 10E
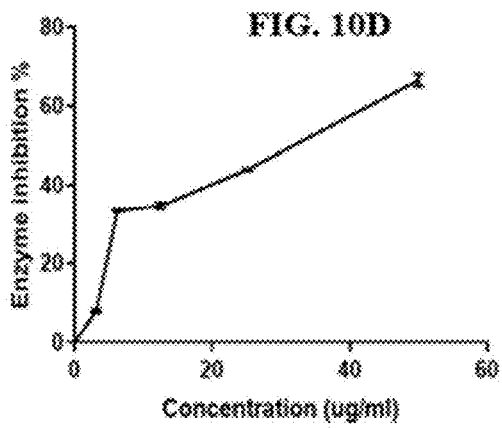 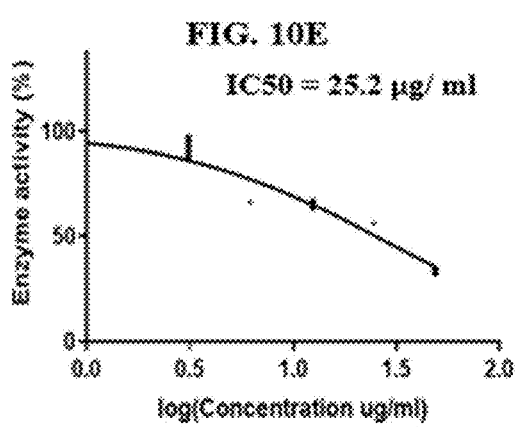
FIG. 10 F     FIG. 10 G

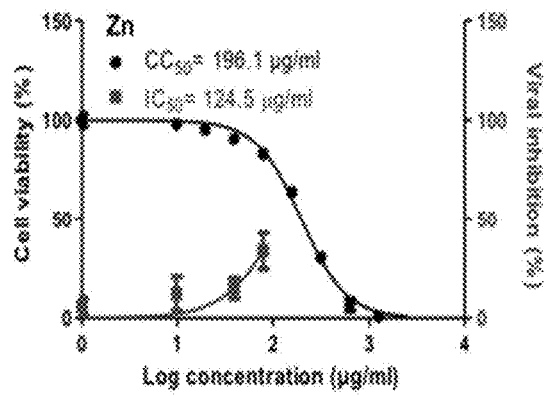 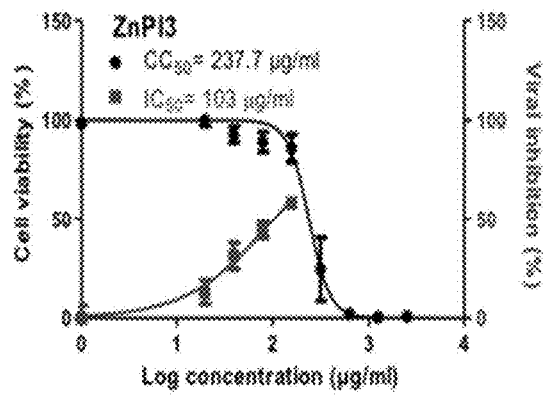

FIG. 11A  FIG. 11B

| Species | Reference body weight (kg) | Working weight range (kg) | Body surface area (m²) | To convert dose in mg/kg to dose in mg/m², multiply by K_m | To convert animal dose in mg/kg to HED in mg/kg, either | |
|---|---|---|---|---|---|---|
| | | | | | Divide animal dose by | Multiply animal dose by |
| Human | 60 | - | 1.62 | 37 | - | - |
| Mouse | 0.02 | 0.011-0.034 | 0.007 | 3 | 12.3 | 0.081 |
| Hamster | 0.08 | 0.047-0.157 | 0.016 | 5 | 7.4 | 0.135 |
| Rat | 0.15 | 0.08-0.27 | 0.025 | 6 | 6.2 | 0.162 |
| Ferret | 0.30 | 0.16-0.54 | 0.043 | 7 | 5.3 | 0.189 |
| Guinea pig | 0.40 | 0.208-0.700 | 0.05 | 8 | 4.6 | 0.216 |
| Rabbit | 1.8 | 0.90-3.0 | 0.15 | 12 | 3.1 | 0.324 |
| Dog | 10 | 5-17 | 0.50 | 20 | 1.8 | 0.541 |
| Monkeys (rhesus) | 3 | 1.4-4.9 | 0.25 | 12 | 3.1 | 0.324 |
| Marmoset | 0.35 | 0.14-0.72 | 0.06 | 6 | 6.2 | 0.162 |
| Squirrel monkey | 0.60 | 0.29-0.97 | 0.09 | 7 | 5.3 | 0.189 |
| Baboon | 12 | 7-23 | 0.60 | 20 | 1.8 | 0.541 |
| Micro pig | 20 | 10-33 | 0.74 | 27 | 1.4 | 0.730 |
| Mini pig | 40 | 25-64 | 1.14 | 35 | 1.1 | 0.946 |

FIG. 12

ANTI-SARS COV-2 INHIBITORS BY DUAL VIRAL-HOST TARGETING

TECHNICAL FIELD

The present invention relates to novel anti-SARS-CoV-2 agents.

BACKGROUND OF THE INVENTION

Coronavirus pandemic disease 2019 (COVID-19) is an emerging public health problem that is caused by severe acute respiratory syndrome coronavirus 2 (SARS-CoV-2) [1]. The emergence of new severe acute respiratory syndrome coronavirus 2 (SARS-CoV-2) caused dramatic health, social and economic threats to the globe, which may extend for several years following this pandemic. With this threat, the expectation of a future outbreak, and the shortage of anti-viral drugs, scientists were challenged to develop novel antiviral drugs.

Several antiviral drugs have been proposed including those targeting the viral or host proteins [2], neutralizing antibodies that target SARS-CoV-2 [3], repurposing of other antiviral drugs used for the treatment of SARS and MERS [4]. Further, some marketed drugs including hydroxychloroquine, lopinavir, chloroquine and remdesivir were evaluated [5-7]. However, the infection continues to be extremely challenging, the cases still increasing and no effective treatment was announced [8]. Therefore, there is an urgent need for the design and development of novel drugs with promising anti-SARS-CoV-2 activity. SARS-CoV-2 is an envelope virus [9] that requires two critical proteases, the main protease ($M^{pro}$) and papain-like protease (PLpro) to complete its life cycle [10]. Both proteases are essential for SARS-CoV-2 replication [11], which renders them important targets for the development of anti-SARS-CoV-2 drugs. $M^{pro}$ proteolytically cleaves the overlapping pp1a and pp1ab polyproteins to functional proteins, which is critical for viral replication [12]. PLpro recognizes the C-terminal sequence of ubiquitin, and hence inhibits the host-cell deubiquitinases [13]. In addition, viral fusion requires the cleavage of spike glycoprotein [14], which is facilitated by the action of human furin protease [15]. Viral fusion to cell membrane is mediated by the cleavage at S1/S2 site of the S protein following the action of human furin protease [16]. This furin-like cleavage site, is responsible for the high infection and spread rates of the virus [17].

This process is characteristic to SARS-CoV-2 when compared to other coronaviruses [15]. Furin protease belongs to proprotein/prohormone convertases (PCs) family that is ubiquitously expressed in humans [18]. This makes human furin protease an important target, particularly to overcome future evolved resistance by the virus itself.

The availability of SARS-CoV-2 $M^{pro}$ crystal structures and its ligand-binding complexes [1][19] enhanced the discovery and design of novel inhibitors following computational techniques. Reported herein for the first time are selective SARS-CoV-2 inhibitors exhibiting antiviral activity and excellent safety profile.

SUMMARY OF THE EMBODIMENTS

In representative embodiments, the invention is directed at novel compounds as selective inhibitors of SARS-CoV-2.

Disclosed herein is compound 7 for treating or preventing SARS-CoV-2 infection, comprising administering an effective amount of the compound to a patient carrying SARS-CoV-2.

In certain embodiments, disclosed herein is compound 13, as well as methods comprising administering an effective amount of the compound 13 to a patient carrying SARS-CoV-2.

In further embodiments, provided herein is compound 13M, and methods of treatment comprising administering an effective amount of the compound 13M to a patient carrying SARS-CoV-2.

Further disclosed is a method of treating a subject afflicted by SARS-CoV-2, comprising administering to the subject in need thereof a therapeutically effective amount of the compound 7, a pharmaceutically acceptable salt thereof, and one or more pharmaceutical excipients.

In certain embodiments, herein provided is a method_of treating a subject afflicted by SARS-CoV-2, the method comprising administering to the subject a therapeutically effective amount of the compound 13, a pharmaceutically acceptable salt thereof, and one or more pharmaceutical excipients.

In certain embodiments, disclosed is a method_of treating a subject afflicted by SARS-CoV-2, the method comprising administering to the subject in need thereof a therapeutically effective amount of the compound 13M, a pharmaceutically acceptable salt thereof, and one or more pharmaceutical excipients.

In certain embodiments, disclosed herein is a kit for treating a subject with SARS-CoV-2, comprising the compounds of the present invention, or a pharmaceutically acceptable salt thereof, and one or more pharmaceutical excipients.

BRIEF DESCRIPTION OF THE FIGURES

The invention can be better understood with reference to the following figures and description.

FIG. 1 illustrates compound supplier ID and the inhibition activity of the candidate 16 compounds against SARS-CoV-2 proteases $M^{pro}$ and PLpro.

FIG. 2 illustrates the inhibition activity and $IC_{50}$ values of compounds 7 and 13 within the binding active site of SARS-CoV-2 $M^{pro}$, PLpro proteases and human furin protease.

FIG. 3A is a graphical representation of screening the inhibition activity of the 16 candidate compounds against SARS-CoV-2 $M^{pro}$. FIG. 3B is a graphical representation of the $IC_{50}$ calculation of compound 13 against SARS-CoV-2 $M^{pro}$. FIG. 3C is a graphical representation of the $IC_{50}$ calculation of compound 7 against SARS-CoV-2 $M^{pro}$. FIG. 3D is a graphical representation of screening the inhibition activity of the 16 candidate compounds against SARS-CoV-2 PLpro. FIG. 3E is a graphical representation of the $IC_{50}$ calculation of compound 13 against SARS-CoV-2 PLpro. FIG. 3F is a graphical representation of the $IC_{50}$ calculation of compound 7 against SARS-CoV-2 PLpro. The data was analyzed using one-way ANOVA and statistical significance was calculated with Bonferroni's multiple comparisons test and significance level indicated by asterisks (*, P<0.05; , P<0.01: *, P<0.001; ****, P<0.0001). The data display the mean of the percentage of the enzyme inhibition±SEM of 3 replicas.

FIG. 4A is a graphical representation of inhibition activity of compounds on furin protease. FIG. 4B is a graphical representation of the $IC_{50}$ calculation of compound 13 against human furin protease.

FIG. 4C is a graphical representation of the $IC_{50}$ calculation of compound 7 against human furin protease. The data display the mean of the percentage of the enzyme inhibition±SEM of 3 replicas.

FIG. 7A is a graphical representation of the $IC_{50}$ calculation of compound 7. FIG. 7B is a graphical representation of the $IC_{50}$ calculation of compound 13. Inhibitory concentration 50% ($IC_{50}$) values were calculated using nonlinear regression analysis by plotting log inhibitor concentration versus normalized response (variable slope). The data display the mean of cell viability percentage±SEM of 4 replicas.

FIG. 8A is a graphical representation of the inhibition activity of compounds 7 and 13 on mammalian cells. FIG. 8B is a graphical representation of the $IC_{50}$ calculation of compound 7 and 13 against normal human mammalian cells. The data display the mean of cell viability percentage±SEM of 3 replicas.

FIGS. 10A-10G illustrate the in vitro and enzyme inhibition activity of compound 13M against SARS-CoV-2. FIG. 10A is a graphical representation of in vitro antiviral activity. FIGS. 10B and 10C are graphical representations of $M^{pro}$ inhibition activity. FIGS. 10D and 10E are graphical representations of Furin enzyme inhibition activity. FIGS. 10F and 10G are graphical representations of TMPRSS2 inhibition activity.

FIGS. 11A and 11B illustrate the in vitro activity of compound 13M formulated as ZnO nanoparticles against SARS-CoV-2. FIG. 11A is a graphical representation of the activity of ZnO nanoparticles against SARS-CoV-2. FIG. 11B is a graphical representation of the activity of 13M-loaded ZnO nanoparticles against SARS-CoV-2.

FIG. 12 summarizes the factors for converting doses between animals and human.

DETAILED DESCRIPTION OF SPECIFIC EMBODIMENTS

Figure 3A:
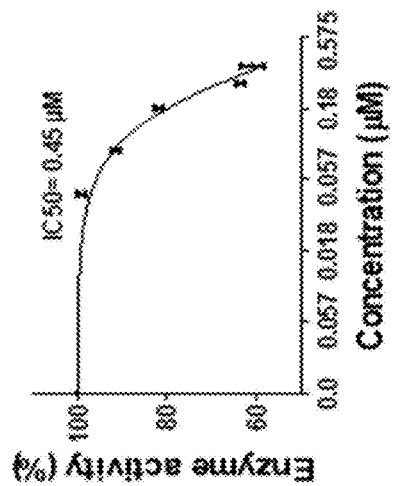
FIGS. 3A-3F summarize inhibition activities and $IC_{50}$ values of compounds 7 and 13.

A study was conducted to identify novel compounds with potential binding activity to SARS-CoV-2 $M^{pro}$ which may find use as inhibitors of SARS-CoV-2. Candidate compounds were selected from a virtual screening of 500,000 compounds. The candidate compounds were evaluated for inhibition activity against SARS-CoV-2 $M^{pro}$ SARS-CoV-2 PLpro, and human furin proteases. A derivative with more significant activity was further evaluated.

Novel compounds 7, 13, and 13M showed dual inhibition activity against SARS-CoV-2. Compounds 7 and 13 showed significant inhibition activity against SARS-CoV-2 infection and no toxicity on mammalian cells at the effective $IC_{50}$, making them potent anti-SARS-CoV-2 agents. Compound 13M exhibited significant inhibition activity against SARS-CoV-2 $M^{pro}$, SARS-CoV-2 furin protease and TMPRSS2 enzyme.

The advantage of these novel compounds derives from their multi-targeting activity, selectivity, in vitro inhibition activity of SARS-CoV-2, and excellent safety profile.

In a first aspect, disclosed herein are three novel SARS-CoV-2 inhibitors for the treatment of COVID-19 infection.

In a first embodiment of the present disclosure, there is provided a compound according to Formula (7):

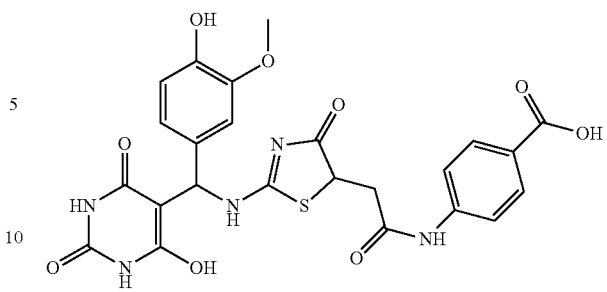

4-[2-(2-{[(6-Hydroxy-2,4-dioxop1,2,3,4-tetrahydro-pyrmidin-5-yl)-[4-hydroxy-3-methoxy-phenyl)-methyl]-amino-4-oxo-4,5-dihydro-thiazol-5-yl)-acetylamino]-benzoic acid (Formula 7).

In a second embodiment of the first aspect, there is provided a compound according to Formula (13):

1,2,5-Oxadiazole-3-carboximidic acid, 4,4'-(methylenediimino)bis,bis[[(2-hydroxyphenyl)methylene]hydrazide (Formula 13).

In a third embodiment of the first aspect, there is provided a compound according to Formula (13M):

Formula (13M)

In a second aspect of the present disclosure, there is provided a method of treating a subject afflicted by SARS-CoV-2. The method includes administering to the subject a therapeutically effective amount of a compound, or a pharmaceutically acceptable salt thereof, and one or more pharmaceutical excipients.

In one exemplary embodiment of the above-mentioned treatment, wherein the compound is a compound according to Formula (7):

Formula (7)

[Chemical structure of Formula (7)]

In a preferred embodiment of the above-mentioned treatment, the compound is a compound according to Formula (13):

Formula (13)

[Chemical structure of Formula (13)]

In another embodiment of the above-mentioned treatment, the provided is a compound according to Formula (13M):

Formula (13M)

[Chemical structure of Formula (13M)]

ZnO nanoparticles loaded with compound 13M showed significant activity against SARS-CoV-2, while providing an employment of lower concentration of the compound (5.5 µg/ml) and wider safety profile.

Compounds described in the present disclosure show enzyme inhibition activity and anti-viral activity against SARS-CoV-2. These compounds had not been reported as SARS-CoV-2 inhibitors at the time of the invention. The results reported herein show these compounds can be useful in the treatment of SARS-CoV-2. Consequently, successful protocols can be translated for therapy of patients afflicted by SARS-CoV-2.

Compositions featuring the aforementioned compounds may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The formulations may conveniently be presented in unit dosage form and may be prepared by any methods well known in the art of pharmacy. The amount of compound which can be combined with a carrier material to produce a single dosage form will vary depending upon the subject being treated, the particular mode of administration. The amount of an active ingredient which can be combined with a carrier material to produce a single dosage form will usually be that amount of the compound which produces a therapeutic effect. Usually, out of one hundred percent, this amount will range from about 1 wt % to about 99 wt % of active ingredient, preferably from about 5 wt % to about 70 wt %, most preferably from about 10 wt % to about 30 wt %.

In certain embodiments, a formulation of the compound includes an excipient selected from the group consisting of cyclodextrins, liposomes, micelle forming agents, e.g., bile acids, and polymeric carriers, e.g., polyesters and polyanhydrides; and an active ingredient that may be the compound and/or one of its pharmaceutically acceptable derivatives. In certain embodiments, an aforementioned formulation renders orally bioavailable a compound or its derivative.

Methods of preparing these formulations or compositions include the step of bringing into association the compound with the carrier and, optionally, one or more accessory ingredients. Usually, the formulations are prepared by uniformly and intimately bringing into association a compound of the present invention with liquid carriers, or finely divided solid carriers, or both, and then, if necessary, shaping the product.

Liquid dosage forms for oral administration of the compound include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents. Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A formulation of the compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also include buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

The tablets, and other solid dosage forms of the formulation of the compound, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Formulations of the pharmaceutical compositions of the compound for rectal or vaginal administration may be presented as a suppository, which may be prepared by the compound with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Dosage forms for the topical or transdermal administration of the compound include powders, sprays, ointments, pastes, creams, lotions, gels, solutions, patches and inhalants. The extract may be mixed under sterile conditions with a pharmaceutically-acceptable carrier, and with any preservatives, buffers, or propellants which may be required. The ointments, pastes, creams and gels may contain, in addition to an extract, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an extract, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Powders and sprays can contain, in addition to an extract, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of the compound to the body. Such dosage forms can be made by dissolving or dispersing an extract in the proper medium. Absorption enhancers can also be used to increase the flux of the extract or dispersing the extract in a polymer matrix or gel.

Pharmaceutical compositions suitable for parenteral administration include one or more components of the compound in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compound may be formulated into pharmaceutically-acceptable dosage forms by conventional methods known to those of skill in the art. The compound may be formulated for administration in any convenient way for use in human or veterinary medicine, by analogy with other pharmaceuticals.

Methods of Treatment of SARS-CoV-2 Infection

The above compound compositions may be used in novel therapeutic methods of treatment in patients afflicted by SARS-CoV-2 infection. The methods include administering to a subject an effective amount of a pharmaceutical compound composition. In representative embodiments, the subject suffers from SARS-CoV-2 infection. In specific embodiments, the SARS-CoV-2 infection can be asymptomatic, or can be symptomatic with different degrees of severity.

The above invention can be used to treat SARS-CoV-2 irrespective of the type of strain, and irrespective of the severity associated with the infection, including, but not limited to moderately symptomatic to severely symptomatic can also be treated.

The phrase, "effective amount" indicates the amount of the compound which is effective, to treat any symptom or aspect of SARS-CoV-2 infection, Effective amounts can be determined routinely. Further guidance on dosages and administration regimens is provided below.

The term "treatment" is used conventionally, e.g., the management or care of a subject for the purpose of combating, alleviating, reducing, relieving, improving, etc., one or more of the symptoms associated with SARS-CoV-2 infection. Administering effective amounts of the compound can treat one or more aspects of SARS-CoV-2 infection, including, but not limited to, inhibiting viral replication; reducing disease progression; stabilizing the disease; prolonging patient survival; enhancing patient's quality of life; reducing adverse symptoms associated with SARS-CoV-2infection; and reducing the frequency, severity, intensity, and/or duration of any of the aforementioned aspects.

The term "subject" in accordance with the present invention, includes, e.g., mammals, such as dogs, cats, horses, rats, mice, monkeys, and humans.

As anticipated above, the compound may be administered by any appropriate route, for example orally, parenterally, topically, or rectally. It will be appreciated that the preferred route may vary with, for example, the condition of the recipient of the compound. In certain embodiments, the extract may be especially suitable for the preparation of pharmaceuticals for intravenous administration, such as intravenous injection or infusion, provided that it does not contain components with serum-precipitating and/or haemagglutinating properties which disturb such an application. The extract may therefore be provided in the form of ampoule preparations which are directed to intravenous administration. In still other embodiments, the method comprises systemic administration of a subject composition to a subject.

Exemplary doses of the compound in the range from about 0.001, 0.01, 0.1, 0.5, 1, 10, 15, 20, 25, 50, 100, 200, 300, 400, 500, 600, or 750 to about 1000 mg/day per kg body weight of the subject. In certain embodiments, the dose of the compound will typically be in the range of about 100 mg/day to about 1000 mg/day per kg body weight of the subject, specifically in the range of about 200 mg/day to about 750 mg/day per kg, and more specifically in the range of about 250 mg/day to about 500 mg/day per kg. In an embodiment, the dose is in the range of about 50 mg/day to about 250 mg/day per kg. In a further embodiment, the dose in the range of about 100 mg/day to about 200 mg/day per kg. In an embodiment, the dose is in the range of about 15 mg/day to 60 mg/day per kg. In a further embodiment, the dose is in the range of about 20 mg/day to 50 mg/day per kg. In an additional embodiment, the dose is in the range of about 25 mg/day to 45 mg/day per kg.

The data obtained from cell culture assays and animal studies may be used in formulating a range of dosage for use in humans. For example, effective dosages achieved in one animal species may be extrapolated for use in another animal, including humans, as illustrated in the conversion table of FIG. 12 where human equivalent dose (HED) dosage factors based on body surface area of other species are reported. [20]. The dosage of any supplement, or alternatively of any components therein, lies preferably within a range of circulating concentrations that include the $ED_{50}$ with little or no toxicity. The dosage may vary within this range depending upon the dosage form employed and the route of administration utilized. For the compound or combinations of the compound and other chemotherapeutic agents, the therapeutically effective dose may be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information may be used to more accurately determine useful doses in humans. Levels in plasma may be measured, for example, by high performance liquid chromatography.

In a third aspect of the present disclosure, there is provided a kit for treating a subject afflicted by SARS-CoV-2, the kit comprising the compound 7, or a pharmaceutically acceptable salt thereof, and one or more pharmaceutical excipients.

The present invention provides kits for novel therapeutic methods in COVID-19 patients. For example, a kit may include one or more pharmaceutical compositions of the compound as described above. The compositions may be pharmaceutical compositions comprising a pharmaceutically acceptable excipient. In other embodiments involving kits, this invention provides a kit including the compound, optionally a chemotherapeutic agent, and optionally instructions for their use in the treatment of SARS-CoV-2. In still other embodiments, the invention provides a kit comprising one more pharmaceutical compositions and one or more devices for accomplishing administration of such compositions. For example, a subject kit may comprise a pharmaceutical composition and catheter for accomplishing direct intraarterial injection of the composition in a patient with SARS-CoV-2 infection. In an embodiment, the device is an intraarterial catheter. Such kits may have a variety of uses, including, for example, therapy, diagnosis, and other applications.

Definitions

As used in this description and the accompanying claims, the following terms shall have the meanings indicated, unless the context otherwise requires:

As used herein, "treatment" is understood to refer to the administration of a drug or drugs to a patient suffering from SARS-CoV-2 infection.

As used herein, the term "therapeutically effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Compound 7 is available at https://pubchem.ncbi.nlm.nih.gov/compound/135936503.

Compound 13 is available at https://pubchem.ncbi.nlm.nih.gov/compound/135699256.

EXPERIMENTAL EXAMPLES

Computational Study

Previously, we ran a virtual screening against SARS-CoV-2 $M^{pro}$ using N3 ligand [21] to build A 3D pharmacophore (PDB: 6LU7). The built pharmacophore was used to screen around 500,000 compounds available in the MCULE and MolPort commercial databases. This was followed by molecular docking against the binding pockets of the enzyme. Only 100 compounds with comparable binding energy were selected and visually re-screened. Out of the 100 compounds, 16 compounds showing the best scoring and binding affinity were re-docked against PLpro and furin proteases. The elected 16 compounds were purchased for further biological activity as described.

Docking-based virtual screening filtered 16 compounds with potential binding activity against SARS-CoV-2 $M^{pro}$, PLpro and human furin proteases The retained 16 molecules were re-docked against PLpro and furin, the molecular docking against PLpro and furin was performed on the crystal structures (PDB: 7JRN) and (PDB: 6HLB), respectively [22, 23].

Compound 7 and 13 Showed Promising Protease Inhibition Activities

Figure 3B:
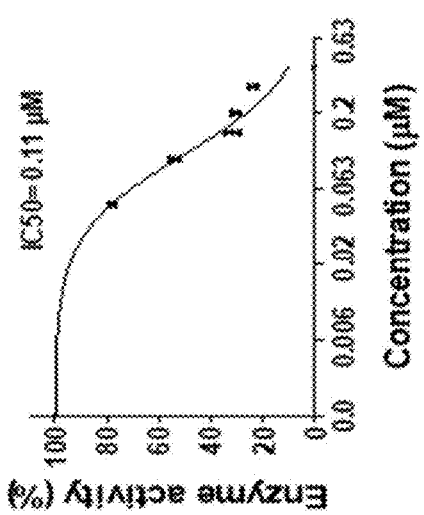
Figure 3C:
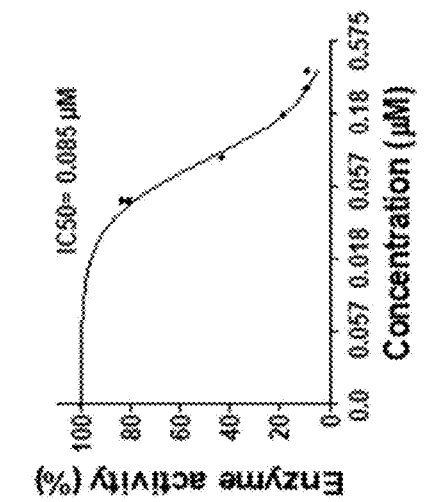

The 16 compounds predicted with potential binding activity to SARS-CoV-2 $M^{pro}$ following virtual screening were screened against SARS-CoV-2 $M^{pro}$ enzyme compared to positive control (FIG. 1 and FIG. 3A). Only compound 13 showed potent inhibition activity (69.8%±3.29, P value<0.0001) against $M^{pro}$ enzyme, while compound 7 and compound 1 showed partial inhibition activity with inhibition percentage 31±2 and 26.44±1.9, respectively (FIG. 3A). Following the primary screening, compounds 7 and 13 were further tested in dose-response curve. The data showed that the $IC_{50}$ of compound 13 and 7 were 0.11 and 0.45 µM, respectively (FIG. 3B and FIG. 3C). These results indicated that both compounds, and particularly 13, are the most potent against SARS-CoV-2 $M^{pro}$.

Figure 3D:
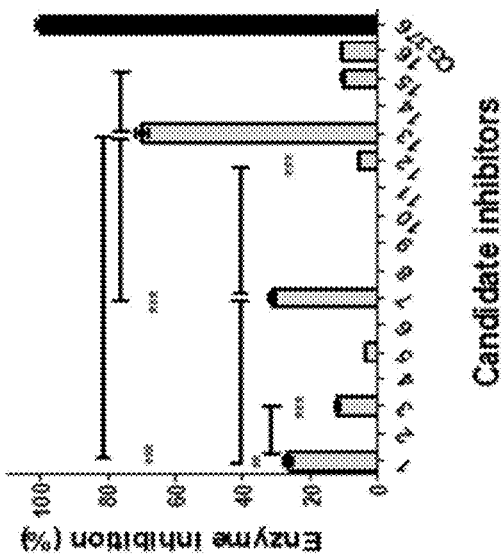
Figure 3E:
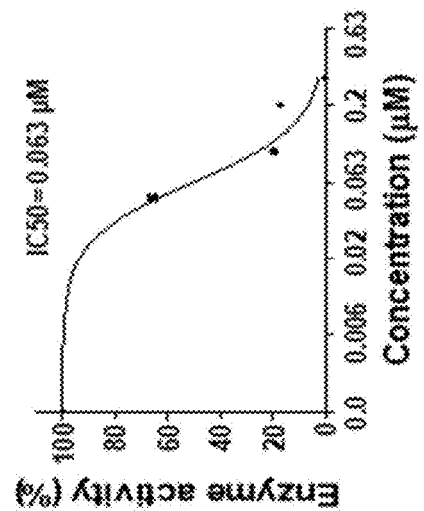
Figure 3F:
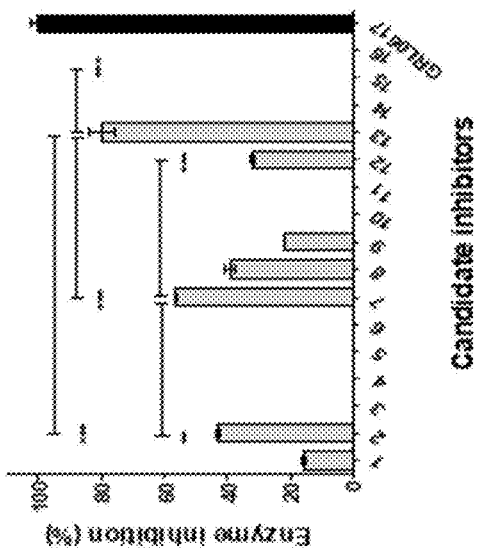

The inhibition activity of the 16 compounds was further tested against SARS-CoV-2 PLpro (FIG. 1 and FIG. 3D). Interestingly, compound 13 showed 80%±4 (P value<0.0001) inhibition activity, while compound 7 exerted 56.4%±0.3 (P value<0.0001) inhibition activity (FIG. 3D). Compound 1, 2, 8, 9 and 12 showed lower inhibition activity of not more than 40% (FIG. 3D). On the other hand, despite the reported anti-HIV activity of compound 14 [24], it showed no activity against any of SARS-CoV-2 proteases. In order to calculate the $IC_{50}$ of both compounds 7 and 13, a dose response curve was performed. The $IC_{50}$ of compounds 13 and 7 were 0.063 and 0.085 µM, respectively (FIG. 3E and FIG. 3F).

Figure 4A:
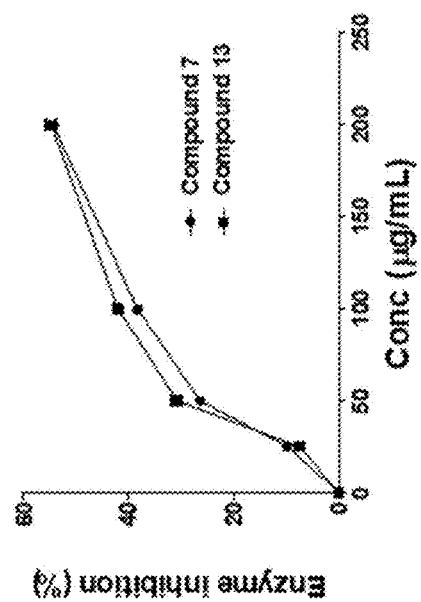
FIGS. 4A-4C illustrate compound inhibition activity against human furin protease.
Figure 4B:
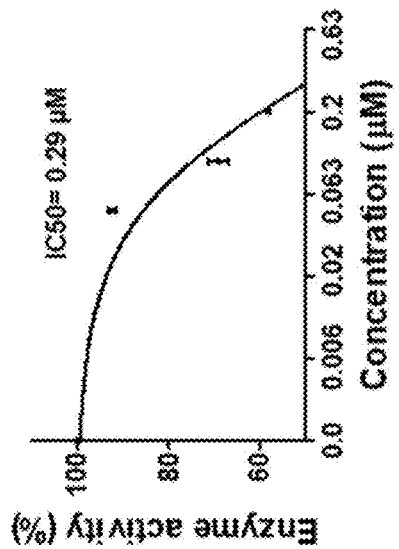
Figure 4C:
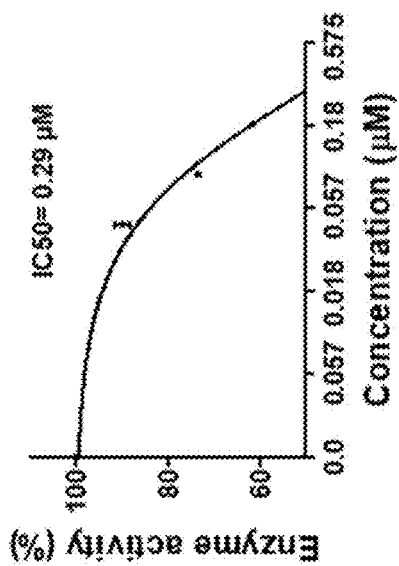

Compound 7 and 13 were further evaluated against human furin protease (FIG. 4A). The data indicated that compounds 7 and 13 showed potential inhibition activity against the enzyme with $IC_{50}$ 0.29 µM (FIG. 4B and FIG. 4C).

Figure 5:
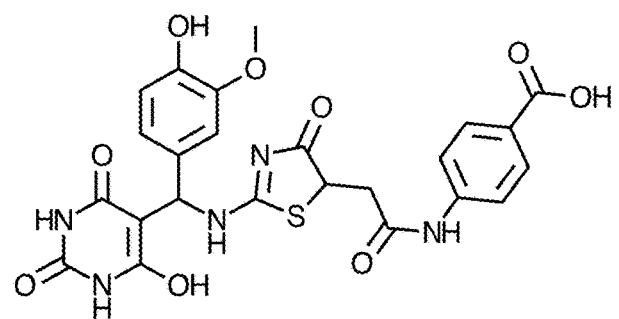
FIG. 5 illustrates compound 7.
Figure 6:
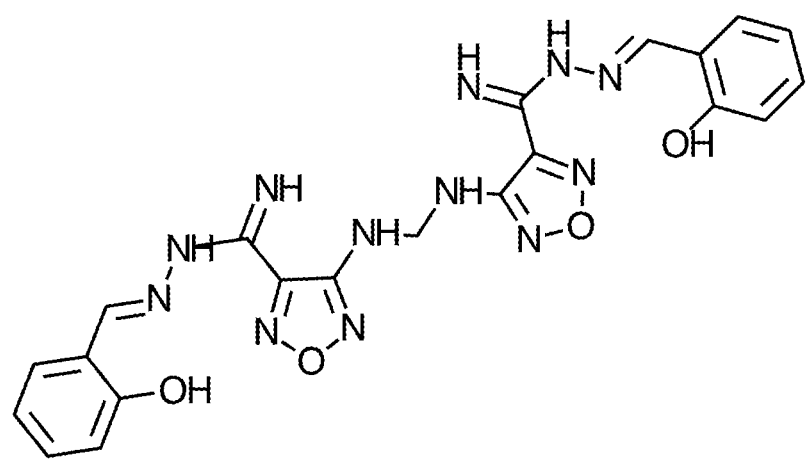
FIG. 6 illustrates compound 13.

The aforementioned data indicated that compounds 7 (FIG. 5) and 13 (FIG. 6) showed promising dual inhibition activity against SARS-CoV-2. Compound 13 targeted both viral $M^{pro}$ and PLpro, while compound 7 selectively targeted viral PLpro and both compounds showed promising inhibition activity against human furin protease. The data obtained constitute solid and promising results toward further confirmation by molecular docking, in vitro and in vivo analysis.

Compounds 7 and 13 Showed Significant Anti-SARS-CoV-2 In Vitro

Figures 7A, 7B:
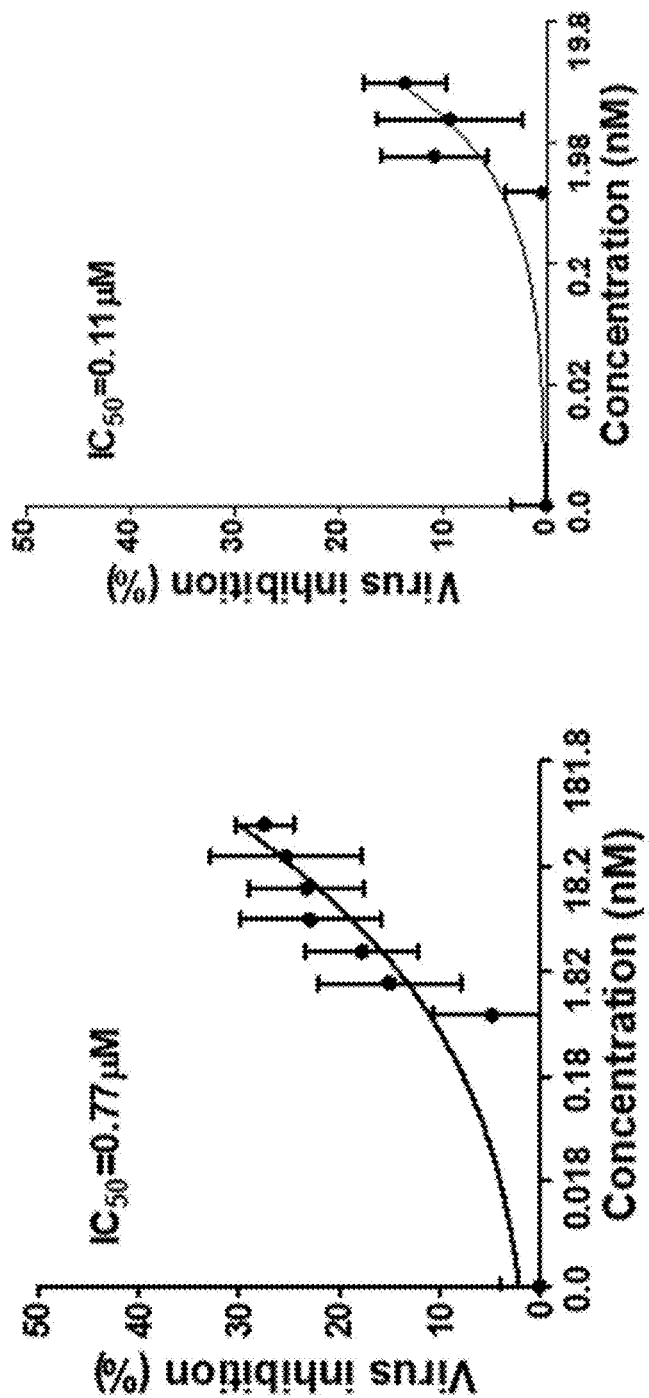
FIGS. 7A and 7B illustrate in vitro antiviral activity of compounds 7 and 13.

The in vitro anti-SARS-CoV-2 activity of compounds 7 and 13 was measured against NRC-03-nhCoV, SARS-CoV-2 strain isolated in Egypt, according to Mostafa et al, 2020 [7]. The antiviral activity was performed by incubating the compounds at different concentrations with co-cultured viral and Vero-E6 cells. Both compounds 7 and 13 showed significant inhibition activity against SARS-CoV-2 at $IC_{50}$ values of 0.77 and 0.11 µM, respectively (FIG. 7A and FIG. 7B).

Compounds 7 and 13 are Safe on Mammalian Cells

Figure 8B:
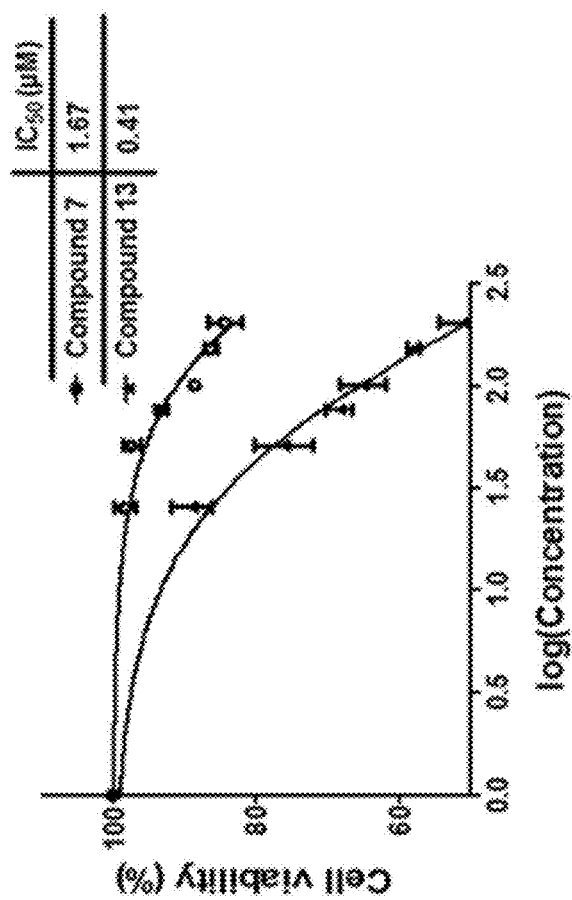
FIGS. 8A and 8B illustrate cytotoxic activities of compounds 7 and 13.
Figure 8A:
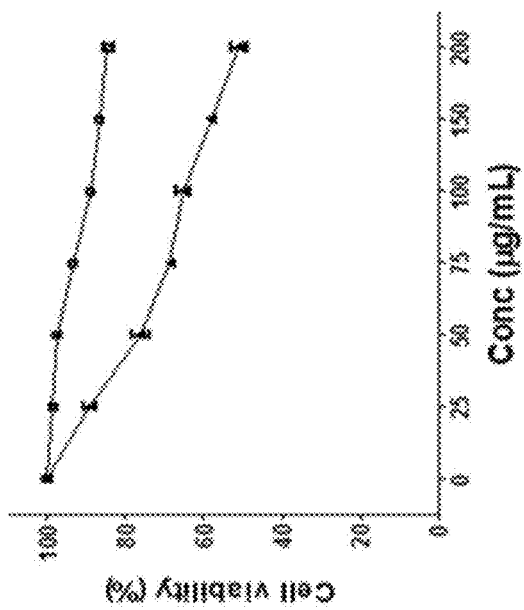
Figure 9:
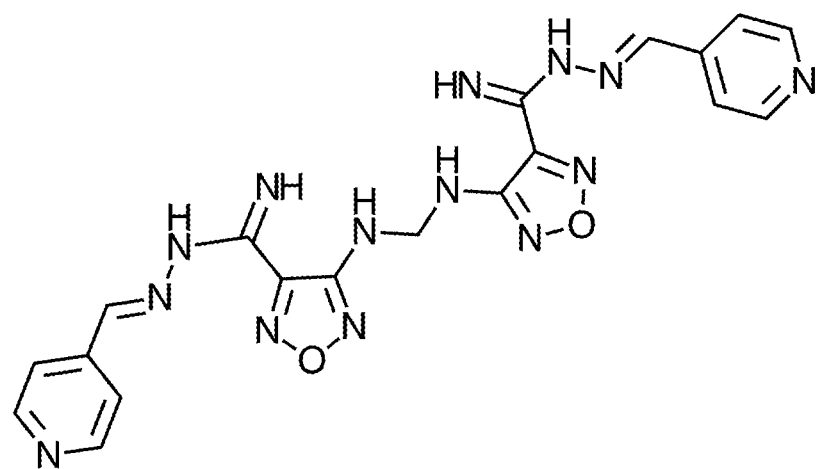
FIG. 9 illustrates Compound 13M.

The cytotoxic activity of compounds 7 and 13 was performed on normal human dermal fibroblast cells line (HDF) using MTT assay. A 50% growth inhibition ($IC_{50}$) value of both compounds was calculated from dose-response curves obtained from three independent experiments (FIG. 8A and FIG. 8B). Compound 13 showed limited toxicity with $IC_{50}$ 0.41 µM, while compound 7 showed no toxicity and with $IC_{50}$ 1.67 µM. The results obtained indicated the safety of both compounds, while showing promising antiviral activity against SARS-CoV-2.

Compound 13M, a derivative of compound 13 was selected following another virual screening and in vitro assay. Compound 13M showed notable antiviral activity in vitro at $IC_{50}$ equal to ~8 µg/ml (FIG. 10A), significant inhibition activity against $M^{pro}$ enzyme with $IC_{50}$ equal to 6.38±1.21 µg/ml (FIG. 10B and FIG. 10C). The inhibition activity of 13M compound was further tested against SARS-CoV-2 furin protease and human TMPRSS2. Interestingly, compound 13M exhibited significant inhibition activity against both enzymes with $IC_{50}$ 40.92±1.049 (FIG. 10D and FIG. 10E) and 25.21±1.107 (FIG. 10F and FIG. 10G), respectively.

Compound 13M was further formulated in ZnO nanoparticles (FIG. 11A and FIG. 11B). Compared to drug-free ZnO nanoparticles (FIG. 11A), 13M-loaded ZnO nanoparticles showed significant antiviral activity (FIG. 11B) with $IC_{50}$ 103 µg/ml. The developed nanoparticles contain lower concentration of the compound ($IC_{50}$ equal to 5.5 µg/ml) and showed wider safety profile ($CC_{50}$ equal to ~238).

Material and Methods

Computational Study

Computational analysis was conducted according to Soliman et al, 2020 [25]. The X-ray crystal structures of SARS-CoV-2 $M^{pro}$, and PLpro proteases (PDB code: 6Y2G and 7JRN, respectively) and human furin protease (PDB: 6HLB) were downloaded from protein data bank (https://www.rcsb.org/) and used for the virtual screening. A library of 500,000 compounds was randomly selected from MCULE database (https://mcule.com/database) and MolPort database (https://www.molport.com) and used for the virtual screening. The interactions between the ligands and proteins was analyzed using a fingerprint scheme based on the interactions of the prepared protein and the co-crystallized ligand. The pharmacophore model was employed as a search query to identify the commercial compounds targeting the binding site, matching at least 5 of the 7 pharmacophore features. The active site of $M^{pro}$, PLpro and furin were identified upon the co-crystallized ligands. Protonation and energy minimization of all compounds were performed using MMFF94X force filed until a RMSD gradient of 0.05 kcal mol$^{-1}$ Å$^{-1}$ was reached. The simulation process created 10 poses, which were sorted according to the lowest energy. The 16 compounds with the highest binding affinity were selected according to their binding within the active pocket and their interactions with the key residues.

Anti-protease Assays

Main Protease ($M^{pro}$) Assay $M^{pro}$ assay was performed using 3CL Protease ($3CL^{pro}$), Untagged (SARS-CoV-2) Assay Kit (CAT #78042-1, BPS Bioscience, San Diego, Calif., USA) following the supplier protocol with minor modifications. In 384 black flat-bottom well plate, 2.5 µl of the tested inhibitors at concentration 100 µg/mL were incubated with 10 µl $3CL^{pro}$ enzyme (1.5 ng/µl) in a reaction buffer made of 20 mM Tris-HCl pH 7.3, 100 mM NaCl, 1 mM EDTA, 0.01% BSA, and 1 mM 1,4-dithio-D,L-threitol (DTT) for 60 min at room temperature with slow shaking. Approximately 12.5 µl of 80 mM $3CL^{pro}$ substrate (Dabcyl-KTSAVLQSGFRKME-Edans fluorogenic substrate) was added followed by incubation for 1 h at room temperature in dark. The fluorescence intensity, developed due to the cleavage of the substrate, was monitored by a microtiter plate-reader (Synergy H1, Biotek Ltd, Winoosk, Vt., USA) at an emission and excitation wavelengths 460 and 360 nm, respectively. Cysteine protease covalent inhibitor (GC376) was employed as positive control according to Fu et al., 2020 [26], while the reactions without inhibitors were employed as negative control. Following the initial screening, the selected hit compounds with significant inhibition activity were prepared in different concentrations (25, 50, 75, 100, 150, and 200 µg/mL) and their inhibition activities were evaluated following the same procedure. The inhibitory activity was plotted against the logarithm of the inhibitor concentrations to calculate the $IC_{50}$.

Papain-like Protease (PLpro) Assay

PLpro assay was performed using recombinant papain-like protease (SARS-CoV-2) assay kit (Cat #79995, BPS Bioscience, San Diego, Calif., USA) following the supplier protocol with minor modification. The enzyme was initially diluted in the supplied buffer containing DTT and 10 µl of the diluted enzyme (1 ng/µL) was added to 2.5 µl of the tested compounds and/or standard inhibitor (1 mM GRL0617) followed by incubation for 30 min at 37° C. according to Gao et al., 2020 [27]. PLpro substrate, Z-Arg-Leu-Arg-Gly-Gly-amino-4-methylcoumarin, was added at concentration 21 µM in dark. The release of amino-4-methylcoumarin fluorophore was monitored after 1 h incubation at excitation and emission λ=360 and 460 nm, respectively. Different concentrations (25, 50, 75, 100, 150, 200 µg/mL) of the tested compounds were evaluated similarly and the $IC_{50}$ was calculated by plotting the percentage of compound inhibitory activity versus the logarithm of the inhibitor concentrations.

Furin Protease Assay

The inhibitory activity of the compounds against furin protease was performed using Furin protease assay kit (Cat #78040, BPS Bioscience, San Diego, Calif., USA) and according to the manufacturer instructions with minor modification. Briefly, different concentrations (25, 50, 100, 200 µg/mL) of the tested compounds were prepared and 10 µl of the tested compounds were added to black flat bottom 96-well plate. Approximately 50 µl recombinant furin enzyme at 0.5 ng/µL was added and the reaction mixture was incubated for 30 min at 37° C. in dark. Following the incubation period, 40 µl furin protease substrate at 5 µM was added to each well and the relative fluorescence value was measured after 1 h with an excitation and emission wavelengths 380 and 460 nm, respectively. Chloromethylketone at 0.5 µM was used as positive control according to Cheng et al., 2020 [28], while the reaction without inhibitor was employed as negative control.

In Vitro Evaluation of Anti-SARS-CoV-2 Activity

The antiviral activity of compounds 7 and 13 was carried out as previously described by Mostafa et al, 2020 [7].

SARS-CoV-2 strain NRC-03-nhCoV isolated in Egypt and deposited in GSAID under the Accession Number: EPI_ISL_430820 was employed in this study. Vero-E6 cells were maintained in Dulbecco's Modified Eagle's medium (DMEM) containing 10% Fetal Bovine Serum (FBS) (Invitrogen) and 1% Penicillin/Streptomycin (pen/strep) antibiotic mixture at 37° C., 5% $CO_2$ for 24 h. The half maximal viral inhibitory ($IC_{50}$) concentrations were determined as previously described [7][16]. Briefly, in 96-well tissue culture plates, $2.4\times10^4$ Vero-E6 cells were distributed in each well and incubated overnight at a humidified 37° C. incubator under 5% $CO_2$. The cell monolayers were then washed once with 1× PBS and subjected to virus adsorption for 1 h at room temperature. The cell monolayers were further overlaid with 50 µl of DMEM containing varying concentrations of the tested compounds. Following incubation at 37° C. in 5% $CO_2$ incubator for 72 h, the cells were fixed with 100 µl of 4% paraformaldehyde for 20 min and stained with 0.1% crystal violet in distilled water for 15 min at RT. The crystal violet dye was then dissolved using 100 µl absolute methanol per well and the optical density of the color is measured at 570 nm using Anthos Zenyth 200rt plate reader (Anthos Labtec Instruments, Heerhugowaard, Netherlands). The $IC_{50}$ of the compound, which is the concentration required to reduce the virus-induced cytopathic effect (CPE) by 50%, relative to the untreated virus control was measured according to the below formula:

$$=[(OD\ \text{test}-OD\ \text{blank})\div(OD\ \text{negative control}-OD\ \text{blank})]\times100$$

Cell Viability Assay

The cytotoxic activities of compounds 7 and 13 were performed using MTT (3-(4, 5-dimethylthiazolyl-2)-2, 5-diphenyltetrazolium bromide) assay according to Soliman, et al, 2020 [29, 30]. MTT assay was performed as follows; 96-well plates were seeded with Normal human dermal fibroblast cells line (HDF, 106-05A, Sigma, EU) at 4000 cells/50 µL and incubated for 24 h at 37° C., 5% $CO_2$. The compounds were added directly to the wells and left for 24 hrs prior to MTT assay. Wells receiving only media were employed as negative control. A 20 µl of sterile filtered MTT reagent in PBS (5 mg/mL) was added to each well. The plates were incubated 4 h and the liquid was then aspirated. DMSO (100 µL) was added to each well to dissolve the formed formazan crystal and incubate for 30 min. The formed purple color was then measured using Multiskan Go machine (spectrophotometer) at 570 nm. Each experiment was repeated 6 times. Empty wells were used as Blank. Cell viability percentage was calculated following the formula, $$\text{Cell viability }(\%)=[(OD\ \text{test}-OD\ \text{blank})\div(OD\ \text{negative control}-OD\ \text{blank})]\times100$$

Statistical Analysis

The data was collected and graphed using GraphPad Prism (5.04, GraphPad Inc., La Jolla, Calif., USA). The enzyme inhibition and cytotoxic activities of the compounds were analyzed by one-way analysis of variance (ANOVA) using Bonferroni's multiple comparisons Test. P-value<0.05 was considered as significant. The data display the mean±SEM of 3-6 replicas.

REFERENCES

[1] Huang C, Wang Y, Li X, Ren L, Zhao J, Hu Y, et al. Clinical features of patients infected with 2019 novel coronavirus in Wuhan, China. The Lancet. 2020; 395:497-506.

[2] Zhang J, Zhou L, Yang Y, Peng W, Wang W, Chen X. Therapeutic and triage strategies for 2019 novel coronavirus disease in fever clinics. The Lancet Respiratory Medicine. 2020; 8:e11-e2.

[3] Li G, De Clercq E. Therapeutic options for the 2019 novel coronavirus (2019-nCoV). Nature Publishing Group; 2020.

[4] Amawi H, Abu Deiab Gal, A Aljabali A A, Dua K, Tambuwala M M. COVID-19 pandemic: an overview of epidemiology, pathogenesis, diagnostics and potential vaccines and therapeutics. Therapeutic delivery. 2020; 11:245-68.

[5] Vankadari N. Arbidol: A potential antiviral drug for the treatment of SARS-CoV-2 by blocking the trimerization of viral spike glycoprotein? International Journal of Antimicrobial Agents. 2020:105998.

[6] Mostafa A, Kandeil A, A. M. M. Elshaier Y, Kutkat O, Moatasim Y, Rashad A A, et al. FDA-Approved Drugs with Potent In Vitro Antiviral Activity against Severe Acute Respiratory Syndrome Coronavirus 2. Pharmaceuticals. 2020; 13:443.

[7] Prevention CfDCa. Coronavirus Disease 2019. CDC Website CDC; 2020.

[8] Lu H. Drug treatment options for the 2019-new coronavirus (2019-nCoV). Bioscience trends. 2020; 14:69-71.

[9] Elfiky A A, Azzam E B. Novel Guanosine Derivatives against MERS CoV polymerase: An in silico perspective. Journal of Biomolecular Structure and Dynamics. 2020:1-9.

[10] Elmezayen A D, Al-Obaidi A, Şahin A T, Yelekçi K. Drug repurposing for coronavirus (COVID-19): in silico screening of known drugs against coronavirus 3CL hydrolase and protease enzymes. Journal of Biomolecular Structure and Dynamics. 2020:1-13.

[11] Ghosh A K, Brindisi M, Shahabi D, Chapman M E, Mesecar A D. Drug Development and Medicinal Chemistry Efforts toward SARS-Coronavirus and Covid-19 Therapeutics. ChemMedChem. 2020.

[12] Hegyi A, Ziebuhr J. Conservation of substrate specificities among coronavirus main proteases. Journal of General Virology. 2002; 83:595-9.

[13] Wu C, Liu Y, Yang Y, Zhang P, Zhong W, Wang Y, et al. Analysis of therapeutic targets for SARS-CoV-2 and discovery of potential drugs by computational methods. Acta Pharmaceutica Sinica B. 2020; 10:766-88.

[14] Walls A C, Park Y-J, Tortorici M A, Wall A, McGuire AT, Veesler D. Structure, function, and antigenicity of the SARS-CoV-2 spike glycoprotein. Cell. 2020.

[15] Coutard B, Valle C, de Lamballerie X, Canard B, Seidah N, Decroly E. The spike glycoprotein of the new coronavirus 2019-nCoV contains a furin-like cleavage site absent in CoV of the same clade. Antiviral Research. 2020; 176:104742.

[16] Xia S, Lan Q, Su S, Wang X, Xu W, Liu Z, et al. The role of furin cleavage site in SARS-CoV-2 spike protein-mediated membrane fusion in the presence or absence of trypsin. Signal Transduction and Targeted Therapy. 2020; 5:92.

[17] Coutard B, Valle C, de Lamballerie X, Canard B, Seidah N G, Decroly E. The spike glycoprotein of the new coronavirus 2019-nCoV contains a furin-like cleavage site absent in CoV of the same clade. Antiviral Research. 2020; 176:104742.

[18] e Greef J C, Slütter B, Anderson M E, Hamlyn R, Landa R O C, McNutt E J, et al. Protective role for the N-terminal domain of α-dystroglycan in Influenza A virus proliferation. Proceedings of the National Academy of Sciences. 2019; 116:11396-401.

[19] Zhang L, Lin D, Sun X, Curth U, Drosten C, Sauerhering L, et al. Crystal structure of SARS-CoV-2 main protease provides a basis for design of improved α-ketoamide inhibitors. Science. 2020; 368:409-12.

[20] Nair, A. B., Jacob S. (2016). A simple practical guide for dose conversion between animal and human. J Basic Clin Pharma 2016, 7:27-31.

[21] Shi X, Cheng Q, Hou T, Han M, Smbatyan G, Lang J E, et al. Genetically Engineered Cell-Derived Nanoparticles for Targeted Breast Cancer Immunotherapy. Molecular Therapy. 2020; 28:536-47.

[22] Coutard B, Valle C, de Lamballerie X, Canard B, Seidah N, Decroly E. The spike glycoprotein of the new coronavirus 2019-nCoV contains a furin-like cleavage site absent in CoV of the same clade. Antiviral research. 2020; 176:104742.

[23] Henrich S, Cameron A, Bourenkov G P, Kiefersauer R, Huber R, Lindberg I, et al. The crystal structure of the proprotein processing proteinase furin explains its stringent specificity. Nature Structural & Molecular Biology. 2003; 10:520-6.

[24] Deng J, Sanchez T, Al-Mawsawi L Q, Dayam R, Yunes R A, Garofalo A, et al. Discovery of structurally diverse HIV-1 integrase inhibitors based on a chalcone pharmacophore. Bioorganic & Medicinal Chemistry. 2007; 15:4985-5002.

[25] Soliman S S M, Hamdy R, Elseginy S A, Gebremariam T, Hamoda A M, Madkour M, et al. Selective inhibition of Rhizopus eumelanin biosynthesis by novel natural product scaffold-based designs caused significant inhibition of fungal pathogenesis. Biochemical Journal. 2020; 477:2489-507.

[26] Fu L, Ye F, Feng Y, Yu F, Wang Q, Wu Y, et al. Both Boceprevir and GC376 efficaciously inhibit SARS-CoV-2 by targeting its main protease. Nature Communications. 2020; 11:4417.

[27] Gao X, Qin B, Chen P, Zhu K, Hou P, Wojdyla J A, et al. Crystal structure of SARS-CoV-2 papain-like protease. Acta Pharmaceutica Sinica B. 2020.

[28] Cheng Y-W, Chao T-L, Li C-L, Chiu M-F, Kao H-C, Wang S-H, et al. Furin Inhibitors Block SARS-CoV-2 Spike Protein Cleavage to Suppress Virus Production and Cytopathic Effects. Cell Reports. 2020; 33:108254.

[29] Soliman S S M, Alhamidi T B, Abdin S, Almehdi A M, Semreen M H, Alhumaidi R B, et al. Effective targeting of breast cancer cells (MCF7) via novel biogenic synthesis of gold nanoparticles using cancer-derived metabolites. PLoS ONE. 2020; 15.

[30] Soliman S S M, Saeed B Q, Elseginy S A, Al-Marzooq F, Ahmady I M, El-Keblawy A A, et al. Critical discovery and synthesis of novel antibacterial and resistance-modifying agents inspired by plant phytochemical defense mechanisms. Chemico-Biological Interactions. 2020.

What is claimed is:

1. The compound according to Formula 13M, or pharmaceutically acceptable salt thereof:

Formula (13M)

2. A pharmaceutical composition, comprising a therapeutically effective amount of the compound of claim 1, or pharmaceutically acceptable salts thereof, and one or more pharmaceutical excipients.

3. A method of treating a subject afflicted by SARS-CoV-2, comprising administering to the subject in need thereof a therapeutically effective amount of Formula 13M or a pharmaceutically acceptable salt thereof and one or more pharmaceutical excipients.

4. The method of claim 3, wherein the subject is a mammal.

5. The method of claim 4, wherein the mammal is a human.

* * * * *